(12) United States Patent
Köhler et al.

(10) Patent No.: US 7,208,640 B2
(45) Date of Patent: Apr. 24, 2007

(54) PROCESS FOR ISOLATING HIGHLY PURE 2-METHOXYPROPENE

(75) Inventors: Günther Köhler, Marl (DE); Volker Brehme, Dortmund (DE); Manfred Neumann, Marl (DE); Clemens Osterholt, Dorsten (DE)

(73) Assignee: Degussa AG, Duesseldorf (DE)

( * ) Notice: Subject to any disclaimer, the term of this patent is extended or adjusted under 35 U.S.C. 154(b) by 35 days.

(21) Appl. No.: 11/116,313

(22) Filed: Apr. 28, 2005

(65) Prior Publication Data

US 2005/0245769 A1   Nov. 3, 2005

(30) Foreign Application Priority Data

Apr. 29, 2004   (DE) .................. 10 2004 021 129

(51) Int. Cl.
*C07C 41/58*  (2006.01)
*C07C 43/15*  (2006.01)
*B01D 3/16*  (2006.01)

(52) U.S. Cl. .................. 568/693; 568/687; 568/594

(58) Field of Classification Search .............. 568/687, 568/693, 594; 203/44, 56, 59, 63
See application file for complete search history.

(56) References Cited

U.S. PATENT DOCUMENTS

| | | | | |
|---|---|---|---|---|
| 3,578,568 A | 5/1971 | Washall | .................. | 203/64 |
| 3,607,003 A | 9/1971 | Stotler | .................. | 423/229 |
| 4,012,289 A | 3/1977 | Haskell | .................. | 203/51 |
| 5,271,835 A | 12/1993 | Gorawara et al. | .......... | 208/228 |
| 5,352,807 A | 10/1994 | Shih | .................. | 549/542 |
| 5,576,465 A | 11/1996 | Kaufhold | .................. | 568/691 |

FOREIGN PATENT DOCUMENTS

| | | |
|---|---|---|
| CZ | 109181 | 4/1962 |
| CZ | 259389 | 10/1988 |
| DE | 1 134 076 | 12/1960 |
| DE | 33 23 823 A1 | 1/1984 |
| DE | 102 33 231 A1 | 2/2004 |
| EP | 0 703 211 A1 | 3/1996 |
| EP | 0 776 879 A1 | 6/1997 |
| RU | 2 110 523 C1 | 3/1997 |
| SU | 662585 | 7/1976 |
| SU | 728902 | 9/1978 |
| WO | WO 01/96269 A1 | 12/2001 |

OTHER PUBLICATIONS

M. Marsi, et al., Tetrahedron Letters, vol. 23, No. 6, pp. 631-634, no month provided/unknown (1982).
R.G. Doerr, et al., J. Am. Chem. Soc., vol. 89, No. 16, pp. 4684-4687, no month provided/unknown (Aug. 30, 1967).
V.V. Beregovykh, et al., Khimiko-Farmatsevticheskij Zhumal, vol. 17, No. 4, pp. 454-459, no month provided/unknown (1983).
B.A. Agre, et al., Vses. Nauchno-Issled. Inst. Org. Sint. Moscow Neftepereabtoka I Neftechimlya, (1), pp. 37-38, no month provided/unknown (1983).
B. Levadie, et al., Analytical Chemistry, vol. 48, No. 11, p. 1656, no month provided/unknown (1976).

*Primary Examiner*—Rosalynd Keys
(74) *Attorney, Agent, or Firm*—Oblon, Spivak, McClelland, Maier & Neustadt, P.C.

(57) ABSTRACT

A process for isolating purified 2-methoxypropene from a mixture which comprises 2,2-dimethoxypropane, 2-methoxypropene, methanol, acetone, and optionally other carbonyl group-containing compounds, which process involves subjecting the mixture to distillation, adding 2-aminoethanol and at least one base as assistants in the distillation, and isolating purified 2-methoxypropene.

27 Claims, No Drawings

PROCESS FOR ISOLATING HIGHLY PURE 2-METHOXYPROPENE

BACKGROUND OF THE INVENTION

1. Field of the Invention

The invention relates to a process for isolating highly pure 2-methoxypropene from crude products or other mixtures which comprise 2,2-dimethoxypropane, 2-methoxypropene, methanol and acetone, with or without other carbonyl compounds, which are obtained, for example, in the synthesis of 2-methoxypropene.

2. Description of the Background

2-Methoxypropene is a valuable intermediate which is required in high purity for the synthesis of active pharmaceutical ingredients. For use in the pharmaceuticals sector, purities of >99.0% are required and limiting values of impurities such as carbonyl compounds of max. 0.2%, especially of max. 0.1%, have to be complied with.

2-Methoxypropene can be prepared particularly advantageously by pyrolyzing 2,2-dimethoxypropane to eliminate methanol and form a crude mixture of 2-methoxypropene, methanol and acetone, and also a series of further impurities. The preparation may be performed either batchwise or continuously, by contacting the 2,2-dimethoxypropane reactant with a catalyst which is present, for example, as a fixed bed or as a contact zone. In the case of the continuous method, the crude product mixture is removed from the reaction zone simultaneously with the reactant feed and the reaction. Preparation processes for 2-methoxypropene via pyrolysis of 2,2-dimethoxypropane are described, for example, in EP 0 703 211 or in EP 0 776 879, WO 2001/096269 or Tetrahedron Letters 23 (6), 631–634, 1982.

Completely different synthetic routes for the preparation of 2-methoxypropene start from 1-propyne or propene and are described, for example, in DE 102 33 231 or in J. Am. Chem. Soc 1967, 89(18), 4684–7.

However, owing to the impurities present therein, especially as a result of its content of carbonyl compounds, e.g. acetone, the 2-methoxypropene obtained by all of these routes does not in any way satisfy the purity requirements for pharmaceutical application. Simple distillative removal is virtually impossible with acceptable technical cost and inconvenience, since binary, ternary or multiple azeotropes form [Beregovykh, V. V.; Andrianove, O. N.; Babich, S. V.; Khimiko-Farnatsevticheskij Zhumal (1983), 17(4), 454–9] and extractive removal of carbonyl compounds is not very effective [Agre, B. A. et al. Vses. Nauchno-Issled. Inst. Org. Sint. Moscow Neftepererabotka i Neftechimiya (Moscow) 1983, (1), 37–38].

According to the prior art, a series of chemical purification processes for aftertreating the crude mixtures is known, in which traces of carbonyl compounds can be removed from the synthesis.

For instance, the patent DE 33 23 823 describes a process for removing impurities (aldehydes and ketones) by the aftertreatment with $NaBH_4$. In order to minimize 0.1–0.2% of impurities to a value of <0.1%, amounts of approx. 10% by weight of $NaBH_4$ and 30–40% by weight of NaOH are needed, which correspondingly increases the complexity of purification and makes the product more expensive.

In a further publication, carbonylic impurities are removed by adding diols which are derivatized as ketals or acetals and can then be removed from the products of value by distillation, as mentioned, for example, in the patent U.S. Pat. No. 3,578,568.

The patent U.S. Pat. No. 4,012,289 describes a further purification process for removing acetone traces by adding sulfolane.

In other patents which describe the purification of acetone-containing product mixtures, acetone traces are removed by air oxidation in the presence of a CuNi catalyst on alumina support (SU 728 902) and (SU 662 585).

A further way of removing acetone traces is described in the patent U.S. Pat. No. 5,352,807 by treating with activated carbon as an adsorbent. Using supercritical $CO_2$, acetone is removed extractively as an impurity according to patent RU 2 110 523. Further processes describe the removal of small amounts of acetone from distillation products by treating with hydroxylamine (patent CS 109 181 and Levadie, Benjamin; Mac Askill, Stephen; Analytical Chemistry 1976, 48(11), 1656 ff.).

U.S. Pat. No. 5,271,835 describes a process for removing sulfuric impurities from light oil streams by treating with alkanolamines, for example methyldiethanolamine, diethanolamine and monoethanolamine. However, traces of polar components such as acetone are removed there mainly on a solid adsorbent which subsequently has to be regenerated again in a costly and inconvenient manner.

According to the patent U.S. Pat. No. 3,607,003, acetone can be removed from hydrogen gas streams which comprise acetone as an impurity using a scrubber, but one which contains an aqueous monoethanolamine solution and is operated at room temperature.

The laid-open specification DE 11 34 076 describes the formation of Schiff bases from carbonyl compounds and primary amines including ethanolamine, by, according to the invention, transferring the imino function from a Schiff base of a preferably low molecular weight carbonyl compound to the carbonyl function of a second carbonyl compound. The target product, the Schiff base of the second carbonyl compound, is removed from the low molecular weight carbonyl compound released. This is effected by crystallizing out and optionally filtration in the case of a sparingly soluble reaction product, or distilling off the newly formed Schiff base, or preferably by distilling off the low molecular weight carbonyl compound. Full retention of the carbonyl compound in the bottoms of the distillation is not described here.

All prior art processes have either the disadvantage that they are technically very complicated, as, for example, in the abovementioned patent DE 11 34 076, or that they do not satisfy the degree of purification required or the efficiency of the removal of carbonyl compounds for a pharmaceutical application of 2-methoxypropene, for which it is important not to exceed an upper limit of max. 0.2%, but preferably max. 0.1%, of acetone.

It is therefore an object of the invention to provide a process, very simple to carry out on the industrial scale, for isolating 2-methoxypropene from 2-methoxypropene-containing mixtures which enables very good yields and provides a highly pure product which may contain a maximum of 0.2%, but preferably max. 0.1%, of carbonyl compound, especially acetone. It should be possible in particular to use crude products or mixtures as the starting material which, in addition to 2,2-dimethoxypropane, may contain methanol, acetone and also further carbonyl compounds as impurities. In particular, it should be possible to use reaction effluents of the 2-methoxypropene synthesis. The process should as far as possible be performable without great additional apparatus complexity and especially the disadvantages of the conventional processes should be avoided.

SUMMARY OF THE INVENTION

These and further objects which are not specified explicitly but which can be derived or discerned from the connections discussed herein are achieved by a process for isolating purified 2-methoxypropene from a mixture which comprises 2,2-dimethoxypropane, 2-methoxypropene, methanol, acetone, and optionally other carbonyl group-containing compounds, said process comprising subjecting said mixture to distillation, adding 2-aminoethanol and at least one base as assistants in the distillation, and isolating said purified 2-methoxypropene.

DETAILED DESCRIPTION OF THE INVENTION

It is possible by employing a distillation process for isolating highly pure 2-methoxypropene from crude products or other mixtures which comprise 2,2-dimethoxypropane, 2-methoxypropene, methanol and acetone, with or without other carbonyl compounds, in which 2-aminoethanol and a base are added as assistants in the distillation, to provide a highly pure product which contains a maximum of 0.2%, but preferably max. 0.1%, of carbonyl compound, especially acetone, in very good yields, and to overcome the disadvantages of the known purification processes.

When reaction effluents of the 2-methoxypropene synthesis are used, they are initially extracted with water in a customary manner to remove the majority of water-soluble by-products, for example, of the acetone.

During the subsequent inventive distillation with addition of 2-aminoethanol and a base as an assistant, the corresponding Schiff bases form from carbonyl compounds and 2-aminoethanol. It is not necessary to distillatively remove the water of reaction from the Schiff base reaction as a special process step.

Preference is given in accordance with the invention to using at least one base selected from the group consisting of alkali metal hydroxide, alkaline earth metal hydroxide, alkali metal carbonate, alkaline earth metal carbonate, alkali metal hydrogencarbonate, alkaline earth metal hydrogencarbonate, alkali metal alkoxide, alkaline earth metal alkoxide, alkali metal carboxylate or alkaline earth metal carboxylate of a mono- or polybasic carboxylic acid having at least 2 carbon atoms, and organic N-containing bases.

The alkali metal or alkaline earth metal used is preferably lithium, sodium, potassium, rubidium, cesium, magnesium, calcium, strontium or barium.

The alkali metal carboxylate or alkaline earth metal carboxylate of a mono- or polybasic carboxylic acid having at least 2 carbon atoms which is used is preferably a carboxylate of the saturated $C_2$ to $C_{18}$ carboxylic acids, of the saturated $C_2$ to $C_6$ dicarboxylic acids, or of the monohydroxy-substituted $C_2$ to $C_6$ mono-, di- or tricarboxylic acids.

The alkali metal alkoxide or alkaline earth metal alkoxide used is preferably an alkoxide of the linear or branched aliphatic $C_1$ to $C_8$ alcohols.

The organic nitrogen-containing base used is preferably one or more compounds of the general formula I, II, III, IV, V, VI or VII:

Formula I:

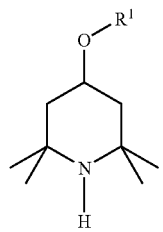

where $R^1$ is hydrogen, an aliphatic or cycloaliphatic, saturated or unsaturated hydrocarbon radical having from 1 to 18 carbon atoms, a saturated or unsaturated, linear or branched acyl radical or an acid radical of a saturated $C_3$ to $C_{20}$ dicarboxylic acid or of an unsaturated $C_4$ to $C_{20}$ dicarboxylic acid or a polyacyl compound or a polysiloxanyl compound of the formula

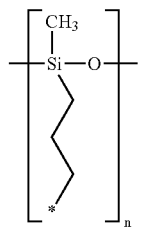

where * indicates where $R^1$ is bonded to O, and n=from 2 to 10

Formula II:

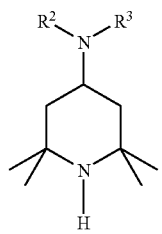

where $R^2$ and $R^3$ may be the same or different and are each hydrogen, an aliphatic or cycloaliphatic, saturated or unsaturated hydrocarbon radical having from 1 to 18 carbon atoms, or one of the two is a saturated or unsaturated, optionally alkyl-substituted alkylene chain having from 2 to 18 carbon atoms which is joined to the nitrogen atom of a second molecule of the formula II, or $R^2$ and $R^3$ together or each are a nitrogen-bonded acid radical of an aliphatic, saturated or unsaturated $C_4$ to $C_5$ dicarboxylic acid which may be $C_1$- to $C_{18}$-alkyl-substituted on one or more carbon atoms, or are together or each a nitrogen-bonded acid radical of an aromatic 1,2-dicarboxylic acid, Formula III:

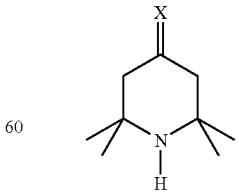

where X=O or N—$R^4$ and $R^4$ is an aliphatic or cycloaliphatic, saturated or unsaturated hydrocarbon radical having from 1 to 18 carbon atoms, Formula IV:

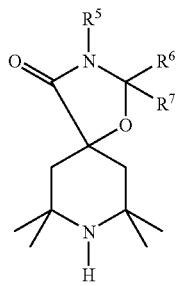

where $R^5$, $R^6$ and $R^7$ may be the same or different and are each hydrogen or an aliphatic or cycloaliphatic, saturated or unsaturated hydrocarbon radical having from 1 to 18 carbon atoms, or $R^6$ and $R^7$ together are an aliphatic, saturated or unsaturated, optionally branched alkylene chain —$(CH_2)_m$— where m=from 2 to 18, $$NR^8R^9R^{10} \qquad \text{Formula V}$$

where $R^8$, $R^9$ and $R^{10}$ may be the same or different and are each an aliphatic, saturated or unsaturated $C_1$- to $C_{18}$-alkyl radical or an aliphatic, saturated or unsaturated $C_5$- to $C_{18}$-cycloalkyl radical and a maximum of two radicals may simultaneously be $C_1$-alkyl, $$HNR^8R^9 \qquad \text{Formula VI}$$

where $R^8$ and $R^9$ are each as defined above and a maximum of one radical may be $C_1$-alkyl, $$N^+R^8R^9R^{10}R^{11}OH^- \qquad \text{Formula VII}$$

where $R^8$, $R^9$, $R^{10}$ and $R^{11}$ may be the same or different and $R^8$, $R^9$, $R^{10}$ are each as defined above and $R^{11}$ is likewise a saturated or unsaturated $C_1$- to $C_{18}$-alkyl radical or an aliphatic, saturated or unsaturated $C_5$- to $C_{18}$-cycloalkyl radical.

However, the nitrogen-containing base used is even more preferably a compound of the formulae I, II, III, IV, V, VI or VII listed above in which

| | |
|---|---|
| $R^1$ = | acryloyl, methacryloyl, 2-alkylacryloyl with a $C_2$- to $C_6$-alkyl group, succinyl, maleoyl, polyacryloyl, the acid radical of a copolymer of ethylene and acrylic acid or hexamethylene-biscarbonyl, |
| $R^2$, $R^3$ = | n-butyl, or |
| $R^2 + R^3$ together = | acid radical of succinic acid, of glutaric acid or of phthalic acid, |
| $R^5$ = | H and m = 11, |
| $R^8$, $R^9$, $R^{10}$ | in formula V are each ethyl, |
| $R^8$, $R^9$, $R^{10}$, $R^{11}$ | in formula VII are each methyl, ethyl or propyl. |

When $R^2+R^3$ together or each form an acid radical of succinic acid, which may be $C_1$ to $C_{18}$-alkyl-substituted on one or more carbon atoms, of glutaric acid, which may be $C_1$ to $C_{18}$-alkyl-substituted on one or more carbon atoms, or of phthalic acid, Formula II can have the following formulae:

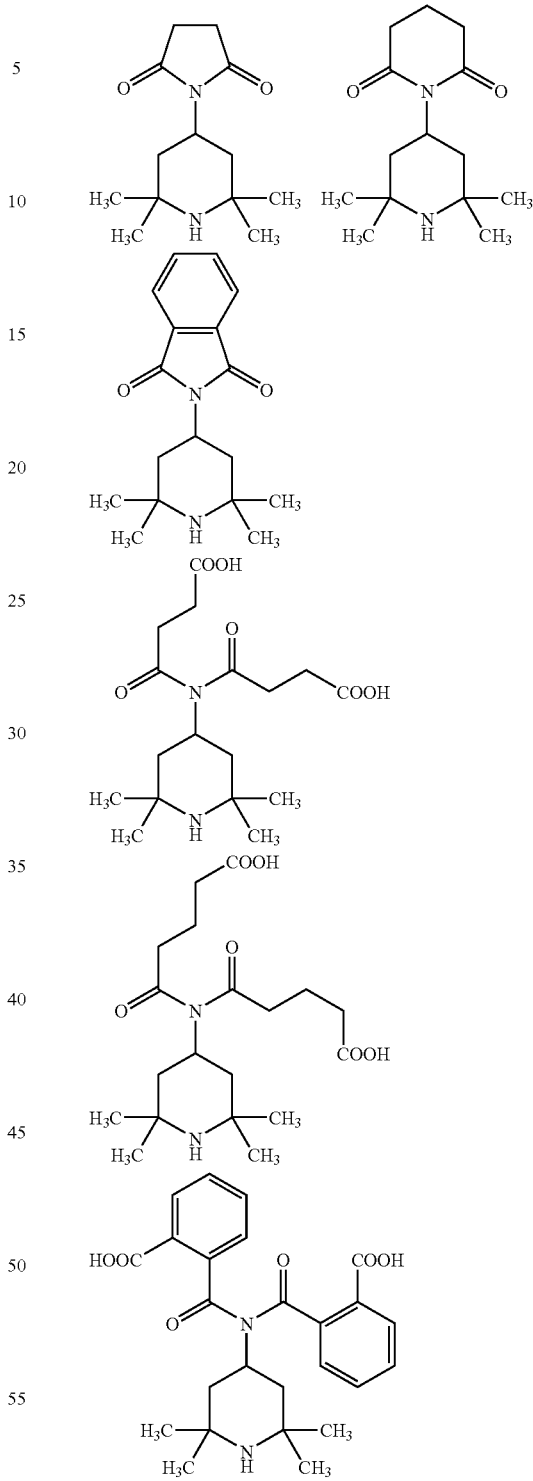

Furthermore, the nitrogen-containing base used is most preferably 3-dodecyl-1-(2,2,6,6-tetramethyl-4-piperidyl)pyrrolidine-2,5-dione (S95), diazabicyclooctane or 4-dimethylaminopyridine.

Preference is given in accordance with the invention to adding 2-aminoethanol and the base, during the distillation, to the distillation bottoms or to the raw material feed for the distillation simultaneously, successively or intermittently. The raw material feed may, as desired, be in the upper, middle or bottom section of the distillation column.

The amount of the aminoethanol added is dependent upon the amount of impurities namely of the carbonyl impurities present. According to the invention, 2-aminoethanol is used preferably in a ratio of from 1 to 10 molar equivalents, more preferably in a ratio of from 1.2 to 5 molar equivalents, in particular from 1.5 to 3 molar equivalents, based on the content of carbonyl compounds.

A preferred amount of base used is a proportion of from 0.5 to 5% by weight, more preferably a proportion of 1 to 4% by weight, based on the starting amount of the raw material feed.

According to the invention, preference is given to selecting a bottom temperature during the distillation of from 30 to 100° C., in particular from 50 to 80° C., and a pressure which is preferably in the range from 100 mbar to 5 bar, but in particular from 900 mbar to 4 bar, but even more preferably at atmospheric pressure.

The distillation process according to the invention may be carried out either continuously or batchwise.

Preference is given in accordance with the invention to using mixtures for the distillation which result from the synthesis of 2-methoxypropene.

Surprisingly, it is possible with the aid of the process according to the invention thus to prepare highly pure 2-methoxypropene by a distillative route. It is possible to achieve purities of >99.0% of 2-methoxypropene and contaminations of carbonyl compounds of a total of <0.1% effortlessly.

The process is very simple to carry out, since, in the first workup step, the crude mixture is extracted in customary plants such as countercurrent extraction columns or stirred tanks. This removes methanol in a conventional manner by extraction. In the second actual workup step, the resulting virtually methanol-free mixture is introduced into a distillation apparatus, preferably into the distillation bottoms, and the crude mixture, together with aminoethanol and a base, is worked up distillatively.

According to the invention, continuous or batchwise distillation plants customary in industry and having preferably approx. 5–20 theoretical plates are used in order to work up the mixture used distillatively. In this workup, traces of low-boiling impurities with the first runnings, the highly pure 2-methoxypropene with the main fraction, and small amounts of water and higher-boiling components, e.g. 2,2-dimethoxypropane, with the final runnings are generally separated from one another distillatively.

In practice, it has been found that preferred process versions for carrying out the latter distillation are in distillation columns having structured distillation packings. Good results are achieved, for example, with a column of from approx. 10 to 15 theoretical plates.

The Schiff base and further high boilers including the base which has likewise been added are retained as the high-boiling distillation residue. From this residue, it is possible if desired to recover both the base and the Schiff base and, from these, the bound 2-aminoethanol by the customary methods known to those skilled in the art, and, if appropriate, to reuse them in the process directly or after further purification.

A great advantage of the process according to the invention is that it can be carried out with apparatus customary in industry, and additionally only comparatively small amounts of assistants have to be added which can additionally readily be removed and optionally regenerated and recycled.

According to the invention, especially the separation of the complex azeotropes occurring in the distillative isolation of 2-methoxypropene is enabled in a particularly simple way. At the same time, the formation of hydroperoxides, otherwise so feared, is suppressed during the distillation of the enol ether by the basicity of the system. In addition, the water which could bring about a dissociation of 2-methoxypropene back to acetone and methanol in the course of the distillation is retained by the process in the bottoms or in the final runnings of the distillation.

The process according to the invention makes it possible for the first time to distillatively purify 2-methoxypropene with economically acceptable cost and inconvenience and the abovementioned high degrees of purity for pharmaceutical applications.

The examples described below are intended to further illustrate the invention but not to restrict it.

EXAMPLE 1

After conventional aqueous extraction of a reaction mixture which stems from the synthesis of 2-methoxypropene starting from 2,2-dimethoxypropane, for example according to EP 0 703 211, a crude mixture is present which has, for example, a composition of the following components, in % by weight:

| | |
|---|---|
| water | 0.13% |
| methanol | 0.14% |
| acetone | 2.64% |
| 2-methoxypropene (MOP) | 65.6% |
| 2,2-dimethoxypropane (DMP) | 31.5% |

Approx. 5% by weight of aminoethanol and approx. 2% by weight of 3-dodecyl-1-(2,2,6,6-tetramethyl-4-piperidyl) pyrrolidine-2,5-dione (S 95, CAS 79720-19-7) as a base were added to the distillation bottoms of the purifying distillation (bottoms). This mixture was fractionally distilled with the aid of a distillation column having 15 theoretical plates.

| | Distillation: | | | | | |
|---|---|---|---|---|---|---|
| | Mass [kg] | Water | MeOH | Acetone | 2-MOP | 2,2-DMP |
| | | | Content in GC area % | | | |
| Crude mixture | 15 | | | | | |
| S 95 addition | 0.30 | | | | | |
| 2-Aminoethanol addition | 0.75 | | | | | |
| Bottoms | 15 | 0.13 | 0.14 | 2.64 | 65.56 | 31.53 |
| Fraction 1 | 0.80 | 0.01 | 1.07 | 0.04 | 57.45 | 40.77 |
| Fractions 2–9 | 8.5 | 0.06 | 0.01 | 0.05 | 99.8 | <0.01 |
| Fraction 10 | 4.90 | 0.37 | 0.03 | 0.18 | 1.28 | 98.01 |
| Residue | 1.80 | | | | | |

Conditions:

| Fractions | Temperatures in [° C.] | | Reflux ratio | Pressure |
|---|---|---|---|---|
| | Bottoms | Tops | R:W[1)] | Mbar |
| 1 | 53 | 34 | 1:1 | 1000 |
| 2–9 | 59 | 35 | 6:1 | 1000 |
| 10 | 65 | 35 | 6:1 | 1000 |

[1)]R:W = reflux:withdrawal amount [in parts by volume]

From 15 kg of starting material which contained a theoretical 9.8 kg of 2-methoxypropene, 8.5 kg of highly pure 2-methoxypropene were obtained with a content of 99.8%, and impurities of acetone, methanol and 2,2-DMP of <0.1%. This corresponds to a distillation yield based on 2-MOP of 87%.

EXAMPLE 2

Instead of the nitrogen base described in Example 1, 2% by weight of 4-amino-2,2,6,6-tetramethylpiperidine were used. The mixture, otherwise identical to in Example 1, was again fractionally distilled in the presence of aminoethanol with the aid of a distillation column having 15 theoretical plates.

Distillation:

| | Mass [kg] | Water | MeOH | Acetone | 2-MOP | 2,2-DMP |
|---|---|---|---|---|---|---|
| | | Content in GC area % | | | | |
| Crude mixture | 15 | | | | | |
| Addition 1: 4-Amino-2,2,6,6-tetramethyl-piperidine | 0.9 | | | | | |
| 2-Aminoethanol addition | 0.3 | | | | | |
| Bottoms | 15 | 0.15 | 0.11 | 2.7 | 65.9 | 31.4 |
| Fraction 1 | 1.1 | 0.06 | 1.2 | 0.1 | 54.4 | 39.8 |
| Fractions 2–9 | 7.9 | 0.03 | 0.01 | 0.09 | 99.7 | <0.01 |
| Fraction 10 | 5.5 | 0.01 | 0.01 | 0.2 | 1.4 | 98.2 |
| Residue | 1.2 | | | | | |

Conditions:

| Fractions | Temperatures in [° C.] | | Reflux ratio | Pressure |
|---|---|---|---|---|
| | Bottoms | Tops | R:W[1)] | Mbar |
| 1 | 53 | 34 | 1:1 | 1000 |
| 2–9 | 60 | 35 | 6:1 | 1000 |
| 10 | 65 | 35 | 6:1 | 1000 |

[1)]R:W = reflux:withdrawal amount [in parts by volume]

From 15 kg of starting material which contained a theoretical 9.8 kg of 2-methoxypropene, 8.5 kg of highly pure 2-methoxypropene were obtained with a content of 99.7%, and impurities of acetone, methanol and 2,2-DMP of <0.1%. This corresponds to a distillation yield based on 2-MOP of 80.4%. The ether peroxide content in the main fraction was <10 ppm.

EXAMPLE 3

Instead of the mixture described in Example 1, distillation was effected in the presence of the additives 2-aminoethanol and $K_2CO_3$. The mixture, otherwise identical to in Example 1, was again fractionally distilled with the aid of a distillation column having 15 theoretical plates.

Distillation:

| | Mass [kg] | Water | MeOH | Acetone | 2-MOP | 2,2-DMP |
|---|---|---|---|---|---|---|
| | | Content in GC area % | | | | |
| Crude mixture | 15 | | | | | |
| Addition 1: Aminoethanol | 0.90 | | | | | |
| Addition 2: $K_2CO_3$ | 0.30 | | | | | |
| Bottoms | 15 | 0.15 | 0.1 | 2.7 | 65.9 | 31.4 |
| Fraction 1 | 1.1 | 0.2 | 1.3 | 0.2 | 58.8 | 38.4 |
| Fractions 2–9 | 7.4 | 0.11 | 0.4 | 0.15 | 99.4 | <0.01 |
| Fraction 10 | 5.8 | 0.01 | 0.01 | 0.1 | 1.9 | 98.0 |
| Residue | 0.7 | | | | | |

Conditions:

| Fractions | Temperatures in [° C.] | | Reflux ratio | Pressure |
|---|---|---|---|---|
| | Bottoms | Tops | R:W[1)] | mbar |
| 1 | 53 | 34 | 1:1 | 1000 |
| 2–9 | 60 | 35 | 6:1 | 1000 |
| 10 | 65 | 35 | 6:1 | 1000 |

[1)]R:W = reflux:withdrawal amount [in parts by volume]

From 15 kg of starting material which contained a theoretical 9.8 kg of 2-methoxypropene, 7.4 kg of highly pure 2-methoxypropene (fraction 2–9) having a content of 99.4% were obtained. This corresponds to a distillation yield based on 2-MOP of 75.1%. The ether peroxide content in the main fraction was <20 ppm.

The disclosure of German application 10 2004 021 129.9, filed Apr. 29, 2004, whose priority date is claimed herein, is hereby incorporated by reference.

The invention claimed is:

1. A process for isolating purified 2-methoxypropene from a mixture which comprises 2,2-dimethoxypropane, 2-methoxypropene, methanol, acetone, and optionally other carbonyl group-containing compounds, said process comprising subjecting said mixture to distillation, adding 2-aminoethanol and at least one base as assistants in the distillation, and isolating said purified 2-methoxypropene.

2. The process of claim 1, wherein said at least one base is selected from the group consisting of alkali metal hydroxide, alkaline earth metal hydroxide, alkali metal carbonate, alkaline earth metal carbonate, alkali metal hydrogencarbonate, alkaline earth metal hydrogencarbonate, alkali metal alkoxide, alkaline earth metal alkoxide, alkali metal carboxylate or alkaline earth metal carboxylate of a mono- or polybasic carboxylic acid having at least 2 carbon atoms, and organic N-containing bases.

3. The process of claim 2, wherein the alkali metal or alkaline earth metal is lithium, sodium, potassium, rubidium, cesium, magnesium, calcium, strontium or barium.

4. The process of claim 2, wherein the at least one base is selected from the group consisting of carboxylates of: the saturated $C_2$ to $C_{18}$ carboxylic acids, the saturated $C_2$ to $C_6$ dicarboxylic acids, and the monohydroxy-substituted $C_2$ to $C_6$ mono-, di- or tricarboxylic acids.

5. The process of claim 2, wherein the at least one base is selected from the group consisting of alkoxides of the linear or branched aliphatic $C_1$ to $C_8$ alcohols.

6. The process of claim 2, wherein the at least one base is at least one organic N-containing base selected from the group consisting of compounds of the general formula I, II, III, IV, V, VI and VII:

Formula I:

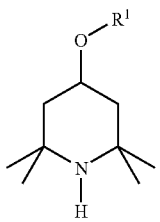

where $R^1$ is hydrogen, an aliphatic or cycloaliphatic, saturated or unsaturated hydrocarbon radical having from 1 to 18 carbon atoms, a saturated or unsaturated, linear or branched acyl radical or an acid radical of a saturated $C_3$ to $C_{20}$ dicarboxylic acid or of an unsaturated $C_4$ to $C_{20}$ dicarboxylic acid or a polyacyl compound or a polysiloxanyl compound of the formula

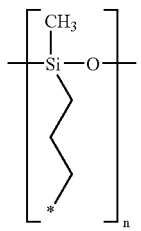

where * indicates where $R^1$ is bonded to O, and n=from 2 to 10

Formula II:

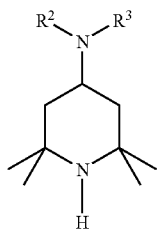

where $R^2$ and $R^3$ may be the same or different and are each hydrogen, an aliphatic or cycloaliphatic, saturated or unsaturated hydrocarbon radical having from 1 to 18 carbon atoms, or one of the two is a saturated or unsaturated, optionally alkyl-substituted alkylene chain having from 2 to 18 carbon atoms which is joined to the nitrogen atom of a second molecule of the formula II, or $R^2$ and $R^3$ together or each are a nitrogen-bonded acid radical of an aliphatic, saturated or unsaturated $C_4$ to $C_5$ dicarboxylic acid which may be $C_1$- to $C_{18}$-alkyl-substituted on one or more carbon atoms, or are together or each a nitrogen-bonded acid radical of an aromatic 1,2-dicarboxylic acid, Formula III:

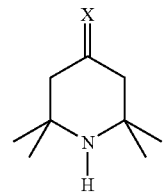

where X═O or N—$R^4$ and $R^4$ is an aliphatic or cycloaliphatic, saturated or unsaturated hydrocarbon radical having from 1 to 18 carbon atoms, Formula IV:

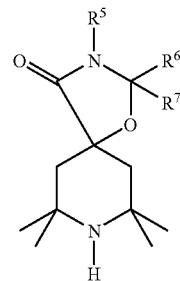

where $R^5$, $R^6$ and $R^7$ may be the same or different and are each hydrogen or an aliphatic or cycloaliphatic, saturated or unsaturated hydrocarbon radical having from 1 to 18 carbon atoms, or $R^6$ and $R^7$ together are an aliphatic, saturated or unsaturated, optionally branched alkylene chain
—$(CH_2)_m$— where m=from 2 to 18, $NR^8R^9R^{10}$          Formula V:

where $R^8$, $R^9$ and $R^{10}$ may be the same or different and are each an aliphatic, saturated or unsaturated $C_1$- to $C_{18}$-alkyl radical or an aliphatic, saturated or unsaturated $C_5$- to $C_{18}$-cycloalkyl radical and a maximum of two radicals may simultaneously be $C_1$-alkyl, $HNR^8R^9$          Formula VI:

where $R^8$ and $R^9$ are each as defined above and a maximum of one radical may be $C_1$-alkyl, $N^+R^8R^9R^{10}R^{11}$ $OH^-$          Formula VII:

where $R^8$, $R^9$, $R^{10}$ and $R^{11}$ may be the same or different and $R^8$, $R^9$, $R^{10}$ are each as defined above and $R^{11}$ is likewise a saturated or unsaturated $C_1$- to $C_{18}$-alkyl radical or an aliphatic, saturated or unsaturated $C_5$- to $C_{18}$-cycloalkyl radical.

7. The process of claim 6, wherein
$R^1$=acryloyl, methacryloyl, 2-alkylacryloyl with a $C_2$- to $C_6$-alkyl group, succinyl, maleoyl, polyacryloyl, the acid radical of a copolymer of ethylene and acrylic acid or hexamethylenebiscarbonyl,
$R^2$, $R^3$=n-butyl, or $R^2+R^3$ together=acid radical of succinic acid, which may be $C_1$ to $C_{18}$-alkyl-substituted on one or more carbon atoms, of glutaric acid, which may be $C_1$ to $C_{18}$-alkyl-substituted on one or more carbon atoms, or of phthalic acid, $R^5$=H and m=11, $R^8$, $R^9$, $R^{10}$ in formula V are each ethyl, $R^8$, $R^9$, $R^{10}$, $R^{11}$ in formula VII are each methyl, ethyl or propyl.

8. The process of claim 1, wherein the base is selected from the group consisting of 3-dodecyl-1-(2,2,6,6-tetramethyl-4-piperidyl)pyrrolidine-2,5-dione, diazabicyclooctane and 4-dimethylaminopyridine.

9. The process of claim 1, wherein 2-aminoethanol and the at least one base are added during the distillation to the distillation bottoms simultaneously, successively or intermittently.

10. The process of claim 1, wherein 2-aminoethanol and the at least one base are added during the distillation to the mixture simultaneously, successively or intermittently.

11. The process of claim 1, wherein 2-aminoethanol, based on the content of carbonyl compound in the mixture, is used in a ratio of from 1 to 10 molar equivalents.

12. The process of claim 11, wherein the ratio is from 1.2 to 5 molar equivalents.

13. The process of claim 12, wherein the ratio is from 1.5 to 3 molar equivalents.

14. The process of claim 1, wherein the amount of base used is in a proportion of from 0.5 to 5% by weight based on the amount of the mixture.

15. The process of claim 14, wherein the amount of base used is in a proportion of 1 to 4% by weight based on the amount of the mixture.

16. The process of claim 1, wherein during the distillation, a bottom temperature of from 30 to 100° C. is selected.

17. The process of claim 16, wherein the bottom temperature is from 50 to 80° C.

18. The process of claim 1, wherein the pressure during the distillation is in the range from 100 mbar to 5 bar.

19. The process of claim 18, wherein the pressure is in the range from 900 mbar to 4 bar.

20. The process of claim 19, wherein the pressure is atmospheric pressure.

21. The process of claim 1, wherein the distillation is carried out continuously or batchwise.

22. The process of claim 1, wherein the mixture is obtained from products of the synthesis of 2-methoxypropene.

23. The process of claim 22, wherein said products are obtained by pyrolyzing 2,2-dimethoxypropane.

24. The process of claim 1, wherein said purified 2-methoxypropene has a purity of greater than 99.0%.

25. The process of claim 1, wherein said purified 2-methoxypropene contains a maximum of 0.2% of carbonyl group-containing compounds.

26. The process of claim 25, wherein said maximum amount is 0.1% of carbonyl group-containing compounds.

27. The process of claim 1, wherein extraction with water to remove water-soluble byproducts is carried out prior to carrying out said distillation.

* * * * *